United States Patent [19]
Ebner et al.

[11] Patent Number: 5,168,090
[45] Date of Patent: Dec. 1, 1992

[54] SHAPED OXIDATION CATALYST STRUCTURES FOR THE PRODUCTION OF MALEIC ANHYDRIDE

[75] Inventors: Jerry R. Ebner, St. Charles; Robert A. Keppel, Chesterfield, both of Mo.

[73] Assignee: Monsanto Company, St. Louis, Mo.

[21] Appl. No.: 812,252

[22] Filed: Dec. 20, 1991

Related U.S. Application Data

[63] Continuation-in-part of Ser. No. 592,722, Oct. 4, 1990, abandoned.

[51] Int. Cl.$^5$ .............. B01J 27/18; B01J 27/198; B01J 27/185
[52] U.S. Cl. ..................... 502/209; 502/527
[58] Field of Search .............. 502/209, 527

[56] References Cited

U.S. PATENT DOCUMENTS

| | | | |
|---|---|---|---|
| 3,347,798 | 10/1967 | Baer et al. | 502/527 X |
| 3,856,824 | 12/1974 | Raffelson et al. | 549/260 |
| 3,862,146 | 1/1975 | Boghosian | 549/259 |
| 3,864,280 | 2/1975 | Schnneider | 502/209 |
| 3,888,886 | 6/1975 | Young et al. | 502/209 X |
| 3,957,627 | 5/1976 | Herrington et al. | 208/216 R |
| 3,966,644 | 6/1976 | Gustafson | 502/527 X |
| 3,980,585 | 9/1976 | Kerr et al. | 502/209 |
| 4,018,709 | 4/1977 | Barone et al. | 502/209 X |
| 4,116,819 | 9/1978 | Frayer et al. | 208/216 R |
| 4,133,777 | 1/1979 | Frayer et al. | 502/527 X |
| 4,178,298 | 12/1979 | Stefani et al. | 502/209 X |
| 4,181,628 | 1/1980 | Stefani et al. | 502/209 |
| 4,187,235 | 2/1980 | Katsumoto et al. | 549/259 |
| 4,251,390 | 2/1981 | Barone et al. | 502/209 |
| 4,282,116 | 8/1981 | Reuter et al. | 502/527 X |
| 4,283,307 | 8/1981 | Barone et al. | 502/209 X |
| 4,312,787 | 1/1982 | Dolhyj et al. | 502/209 |
| 4,315,864 | 2/1982 | Bremer et al. | 502/209 X |
| 4,328,130 | 5/1982 | Kyan | 502/527 X |
| 4,333,853 | 6/1982 | Milberger et al. | 502/209 |
| 4,342,643 | 8/1982 | Kyan | 208/134 |
| 4,370,261 | 1/1983 | Wunder et al. | 502/527 X |
| 4,441,990 | 4/1984 | Huang | 502/527 X |
| 4,562,268 | 12/1985 | Wrobleski et al. | 549/259 |
| 4,632,915 | 12/1986 | Keppel et al. | 502/209 |
| 4,656,157 | 4/1987 | Hofmann et al. | 502/527 X |
| 4,673,664 | 6/1987 | Bambrick | 502/527 X |
| 4,824,819 | 4/1989 | Edwards et al. | 502/209 |

FOREIGN PATENT DOCUMENTS

| | | | |
|---|---|---|---|
| 0037020 | 10/1981 | European Pat. Off. | 502/209 |
| 0098039 | 1/1984 | European Pat. Off. | 502/209 |
| 107274 | 5/1984 | European Pat. Off. | |
| 151912 | 8/1985 | European Pat. Off. | |
| 220933 | 5/1987 | European Pat. Off. | |
| 1373351 | 11/1974 | United Kingdom | |
| 2046118 | 11/1980 | United Kingdom | |
| 2193907 | 2/1988 | United Kingdom | |

OTHER PUBLICATIONS

Kirk-Othmer, *Encyclopedia of Chemical Technology*, 3rd ed., vol. 5, pp. 19 and 20.

Primary Examiner—W. J. Shine
Assistant Examiner—Douglas J. McGinty
Attorney, Agent, or Firm—W. Brooks

[57] ABSTRACT

Shaped oxidation catalyst structures containing catalytic material comprised of mixed oxides of vanadium and phosphorus which are useful for the production of maleic anhydride via the partial oxidation of nonaromatic hydrocarbons, particularly n-butane, in the vapor phase with molecular oxygen or a molecular oxygen-containing gas are provided. Such structures are characterized by exhibiting (a) a geometric volume of from about 30 percent to about 67 percent of that exhibited by the void space-free solid geometric form, (b) an external geometric surface area/geometric volume ratio of at least about 20 cm$^{-1}$, (c) a bulk density of from about 0.4 g/cm$^3$ to about 1.4 g/cm$^3$, and (d) a mechanical resistance sufficient to maintain substantially the structural integrity of the shaped structure under handling and use conditions.

18 Claims, 16 Drawing Sheets

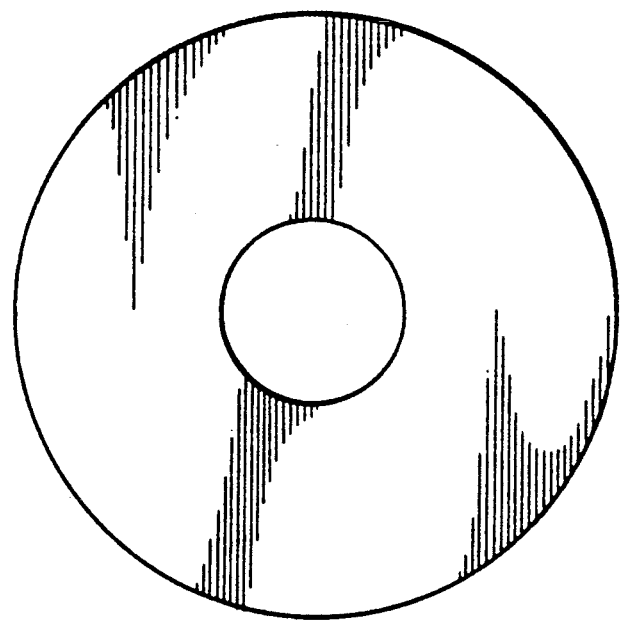
FIG. 4B (COMPARATIVE)
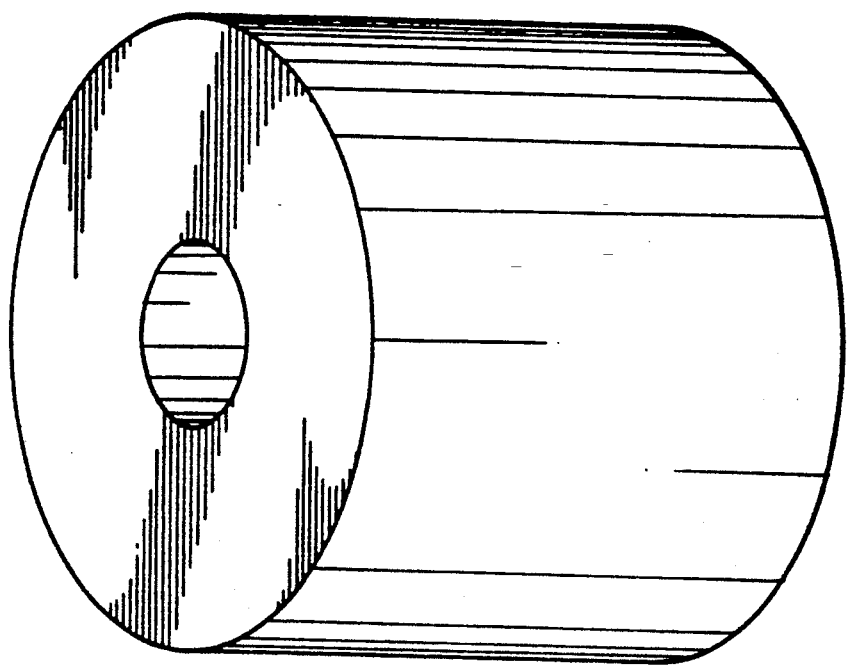
FIG. 4A (COMPARATIVE)

SHAPED OXIDATION CATALYST STRUCTURES FOR THE PRODUCTION OF MALEIC ANHYDRIDE

This is a continuation-in-part, of application Ser. No. 07/592,722, filed on Oct. 4, 1990, abandoned.

BACKGROUND OF THE INVENTION

1. Field of the Invention

This invention relates to shaped oxidation catalyst structures. More particularly, this invention relates to shaped oxidation catalyst structures containing catalytic material comprised of mixed oxides of vanadium and phosphorus which are suitable for the production of maleic anhydride via the partial oxidation of nonaromatic hydrocarbons in the vapor phase with molecular oxygen or a molecular oxygen-containing gas.

2. Description of the Prior Art

The physical form of a catalyst in heterogeneous catalysis is known to be an important factor governing the activity and productivity thereof. In general, a given catalyst exhibits increased activity as the particle size of the catalyst is decreased. However, in fixed-bed reactor systems, a decrease in catalyst particle size results in an increase in pressure drop across the catalyst bed. This phenomenon results from close packing of the catalyst particles in the catalyst bed. And as the pressure drop across the catalyst bed increases, the amount of reactant gas that can be passed through the catalyst bed at a fixed inlet pressure becomes limited. Conversely, as the catalyst particle size is increased to improve pressure drop across the catalyst bed, some loss of catalyst activity results from, inter alia, the effect of lower catalyst charge density, that is, quantity of catalyst per unit of reactor volume.

In an attempt to overcome the difficulties experienced with respect to catalyst activity an productivity and pressure drop across the catalyst bed, a number of catalyst shapes have been described in the prior art.

U.S. Pat. Nos. 4,370,492 and 4,370,261 describe star or ribbed rod catalyst carrier shapes as being useful for supporting active metals for the production of vinyl acetate in the gaseous phase reaction of ethylene with acetic acid and [molecular] oxygen or [molecular] oxygen-containing gases.

U.S. Pat. Nos. 4,342,603 and 4,328,130 describes a hydrocarbon conversion catalyst having substantially the shape of a cylinder having a plurality of longitudinal channels extending radially from the circumference of the cylinder and defining protrusions therebetween. The protrusions are described as having maximum widths greater than the maximum widths of the channels.

U.S. Pat. Nos. 4,133,777 and 4,116,819 describe catalysts in the shape of elongated extrudates having alternating longitudinal grooves and protrusions on the surface. Such catalysts reportedly are useful for hydrodesulfurization of residual petroleum oils, coal liquids, shale oils, and oils from tar sands.

U.S. Pat. No. 3,966,644 describes shaped porous catalysts that are defined as concave geometric cylinders which are polylobal in shape. The catalysts reportedly are useful in the hydrotreating of hydrocarbons with increased catalyst efficiency over conventionally shaped catalysts.

In U.S. Pat. No. 3,957,627, a substantially spherical catalyst having a void center and a hole extending to the external surface is described as being useful for hydrotreating a hydrocarbon feed stock containing compounds with carbon-sulfur bonds, carbon-nitrogen bonds, and/or carbon-oxygen bonds.

U.S. Pat. No. 3,347,798 discloses hollow bead catalysts which reportedly are suitable for use in a wide variety of fluidized bed reactions, for example, in the hydrogenation, oxidation, dehydrogenation, dehydration, polymerization, condensation, amination, reduction of aromatic nitro compounds, cracking, refining and reforming of hydrocarbons, alkylation of hydrocarbons or their derivatives, and also aromatic amino, nitro and aminonitro compounds by reduction or reaction with alcohols, and also the production of alkanolamines, diamines, diphenylamine, and imines.

In spite of the foregoing, however, catalysis remains basically an inexact science, that is, an empirical art unenlightened by rules decreeing certainty and predictability. Thus, the directional effect of catalyst shape on a particular catalytic reaction with a particular catalytic material is not predictable. Primarily, this is due to each catalytic reaction having unique reaction kinetics and the catalyst utilized having unique forming characteristics.

The production of maleic anhydride via the partial oxidation of hydrocarbons in the vapor phase with molecular oxygen or a molecular oxygen-containing gas in the presence of a vanadium phosphorus oxide catalyst is one such reaction. Maleic anhydride is of significant commercial interest throughout the world. It is used alone or in combination with other acids in the manufacture of alkyd and polyester resins. It also is a versatile intermediate for chemical synthesis. Significant quantities of maleic anhydride are produced each year to satisfy these varied needs.

Various oxidation catalysts and oxidation catalyst shapes and techniques have been used in the production of maleic anhydride, particularly the partial oxidation of nonaromatic hydrocarbons having at least four carbon atoms in a straight chain (or cyclic structure). In general, such catalysts contain mixed oxides of vanadium and phosphorus. More particularly, such catalysts wherein the valence of the vanadium is between about +3.8 and +4.8 are considered as being especially well-suited for the production of maleic anhydride from saturated hydrocarbons having at least four carbon atoms in a straight chain. In many instances, such catalysts also contain added promoter elements which are considered to exist in the catalysts as the oxide.

U.S. Pat. No. 4,283,307 describes an oxidation catalyst structure for the production of maleic anhydride which comprises a cylinder having a bore therethrough and is further described as consisting essentially of catalytic material comprised of a phosphorus, vanadium, oxygen complex.

U.S. Pat. Nos. 4,181,628 and 4,178,298 describe (solid) pellets (cylinders) as a suitable oxidation catalyst structure for the production of maleic anhydride.

U.S. Pat. No. 4,632,915 discloses catalysts comprising phosphorus, vanadium and oxygen, and a promoter component containing each of iron and lithium which are useful for the partial oxidation of nonaromatic hydrocarbons, particularly n-butane, with molecular oxygen or a molecular oxygen-containing gas in the vapor phase to produce maleic anhydride in excellent yields.

U.S. Pat. No. 4,562,268 relates to a process for the production of maleic anhydride from nonaromatic hydrocarbons in the presence of a vanadium/phosphorus mixed oxide oxidation catalyst wherein the catalyst exhibits a single pass weight/weight productivity of at least 70 grams of maleic anhydride per kilogram of catalyst per hour.

U.S. Pat. No. 4,333,853 discloses a vanadium/phosphorus mixed oxide catalyst prepared by reducing vanadium substantially in the pentavalent valence state to a tetravalent valence state in the presence of a phosphorus-containing compound and in the absence of a corrosive reducing agent in an organic liquid medium capable of reducing the vanadium to a valence state less than +5, recovering the resultant vanadium/phosphorus mixed oxide catalyst precursor, drying such precursor, and calcining the precursor to obtain the active catalyst. Such catalysts reportedly are effective in the oxidation of $C_4$ hydrocarbons such as n-butane, 1- and 2-butenes, 1,3-butadiene, or mixtures thereof to produce maleic anhydride with selectivities ranging from 58.7% to 68.1% and yields (mol %) ranging from 51.4% to 59.5%.

U.S. Pat. No. 4,315,864 relates to a process for the production of maleic anhydride from normal $C_4$ hydrocarbons in the presence of a vanadium/phosphorus mixed oxide catalyst. The catalyst is prepared by reducing a pentavalent vanadium-containing compound in an olefinic, oxygenated organic liquid medium to a +4 valence in the absence of a corrosive reducing agent, recovering resultant catalyst precursor, drying the catalyst precursor, and calcining the precursor to obtain the active catalyst.

U.S. Pat. No. 4,312,787 describes a catalyst which comprises an inert support and a catalytically active mixed oxide material coating of vanadium and phosphorus or of vanadium, phosphorus, and uranium on the outer surface of the support in an amount greater than 50% to about 80% by weight of the combined support and oxide material. Catalysts within the scope of the claims of the patent were reported to produce maleic anhydride from n-butane in yields ranging from 53% to 62.5%, with selectivities ranging from 57.4% to 67.9%.

In U.S. Pat. No. 4,251,390, a zinc-promoted vanadium-phosphorus-oxygen catalyst is disclosed and claimed. The catalyst is prepared by reducing pentavalent vanadium in a substantially anhydrous organic medium to a lower valent state and digesting the reduced vanadium in the presence of a zinc promoter compound. The resultant catalyst is activated by bringing the catalyst to operating temperatures for the oxidation of n-butane to maleic anhydride at a rate of 5° C. to 10° C. per hour in the presence of a butane-in-air mixture.

In U.S. Pat. No. 4,187,235, a process is described for preparing maleic anhydride from n-butane in the presence of a vanadium-phosphorus-oxygen high surface area catalyst, that is, 10 to 100 square meters per gram ($m^2/g$), as determined by the BET method. The catalyst is prepared by reducing pentavalent vanadium to a valence between +4.0 and +4.6 with a substantially anhydrous primary or secondary alcohol and contacting the reduced vanadium with phosphoric acid, followed by recovering and calcining the resultant vanadium(IV) phosphate compound.

U.S. Pat. No. 4,018,709 discloses a process for the vapor phase oxidation of normal $C_4$ hydrocarbons using catalysts containing vanadium, phosphorus, uranium, or tungsten or a mixture of elements from zinc, chromium, uranium, tungsten, cadmium, nickel, boron, and silicon. In a preferred embodiment, the catalyst also contains an alkali metal or an alkaline earth metal, especially lithium, sodium, magnesium, or barium as active components. Typically, such catalysts are prepared in concentrated (37%) hydrochloric acid.

In U.S. Pat. No. 3,980,585, a process is disclosed for the preparation of maleic anhydride from normal $C_4$ hydrocarbons in the presence of a catalyst containing vanadium, phosphorus, copper, oxygen, tellurium, or a mixture of tellurium and hafnium or uranium or a catalyst containing vanadium, phosphorus, copper, and at least one element selected from the group of tellurium, zirconium, nickel, cerium, tungsten, palladium, silver, manganese, chromium, zinc, molybdenum, rhenium, samarium, lanthanum, hafnium, tantalum, thorium, cobalt, uranium, and tin, optionally (and preferably) with an element from Groups IA (alkali metals) or IIA (alkaline earth metals).

U.S. Pat. No. 3,888,866 discloses a process for the oxidation of n-butane at a temperature from about 300° C. to about 600° C. with a vanadium/phosphorus/oxygen catalyst having a phosphorus/vanadium atom ratio of 0.5-2, promoted or modified with chromium, iron, hafnium, zirconium, lanthanum, and cerium, the promoter metal/vanadium atom ratio being between about 0.0025 and about 1. The catalysts are prepared by refluxing a reaction mixture of vanadium oxide, phosphorus, a hydrogen halide (usually hydrochloric acid), and a specified promoter metal-containing compound. The resultant catalyst precursors are recovered, dried, formed into structures—spheres, for example—and calcined to produce the active catalyst.

U.S. Pat. No. 3,864,280 discloses vanadium/phosphorus mixed oxide catalyst having an intrinsic surface area of from about 7 to about 50 $m^2/g$. The catalysts are prepared by precipitation of a vanadium/phosphorus/oxygen complex from an essentially organic solvent medium in the absence of gross amounts of water. The resultant crystalline precipitate is activated by heating in air, followed by a 1.5 mol % butane-in-air mixture, both at elevated temperatures.

U.S. Pat. No. 3,862,146 discloses a process for the oxidation of n-butane to maleic anhydride in the presence of a vanadium-phosphorus-oxygen catalyst complex, promoted or activated with zinc, bismuth, copper, or lithium activator. The phosphorus/vanadium and activator/vanadium atom ratios are from about 0.5-5 and from about 0.05-0.5, respectively.

U.S. Pat. No. 3,856,824 discloses a process for the production of maleic anhydride by oxidation of saturated aliphatic hydrocarbons in the presence of a catalyst comprising vanadium, phosphorus, iron, oxygen, and added modifier comprising chromium combined with at least one element selected from the group consisting of nickel, boron, silver, cadmium, and barium.

European Patent Application No. 98,039 discloses a process for the preparation of vanadium-phosphorus mixed oxide catalysts, optionally containing an added promoter element selected from the group consisting of Group IA (alkali metals), Group IIA (alkaline earth metals), titanium, chromium, tungsten, niobium, tantalum, manganese, thorium, uranium, cobalt, molybdenum, iron, zinc, hafnium, zirconium, nickel, copper, arsenic, antimony, tellurium, bismuth, tin, germanium, cadmium, and lanthanides, and mixtures thereof. The catalysts, which exhibit a phosphorus/vanadium atom ratio of from about 0.8 to about 1.3 and a promoter/vanadium atom ratio from about 0.01 to about 0.5, are prepared in an organic liquid reaction medium capable of reducing the vanadium to a valence state of approximately +4 to form a nonsolubilized catalyst precursor, contacting the nonsolubilized catalyst precursor-containing organic liquid with water to form a two-phase system having an upper organic liquid phase and a lower nonsolubilized catalyst precursor-containing aqueous phase, drying the catalyst precursor, and calcining the precursor to obtain the active catalyst.

The oxidation catalysts described in the cited references disclose several well-known solid catalyst shapes commonly employed in fixed-bed vapor phase maleic anhydride production processes, for example, spheres or spheroids, tablets, and pellets. And although the prior art catalysts and catalyst shapes generally are successful in producing the desired maleic anhydride product, the commercial utility of a catalyst system and a catalytic process is highly dependent upon the cost of the catalyst employed, the conversion of the reactants, and the yield of the desired product(s), or stated differently, the actual productivity of the catalyst system. In many instances, a reduction in the cost of a catalyst system employed in a given catalytic process on the order of a few cents per kilogram or pound, or a small percent increase in the yield of the desired product, relative to the amount of catalyst required, represents a tremendous economic advantage in a commercial operation. Accordingly, research efforts are continually being made to define new or improved catalyst systems and methods and processes of making new and old catalyst systems to reduce the cost and/or upgrade the activity, selectivity, and/or productivity of such catalyst systems in such catalytic processes. The discovery of the shaped oxidation catalyst structures of the instant invention, therefore, is believed to be a decided advance in the art.

BRIEF DESCRIPTION OF THE DRAWINGS

FIG. 4A illustrates a solid cylindrical structure with a void space as a centrally located bore.

FIG. 4B illustrates, in top elevational view, a solid cylindrical structure with a void space as a centrally located bore.

SUMMARY OF THE INVENTION

Figure 1B:
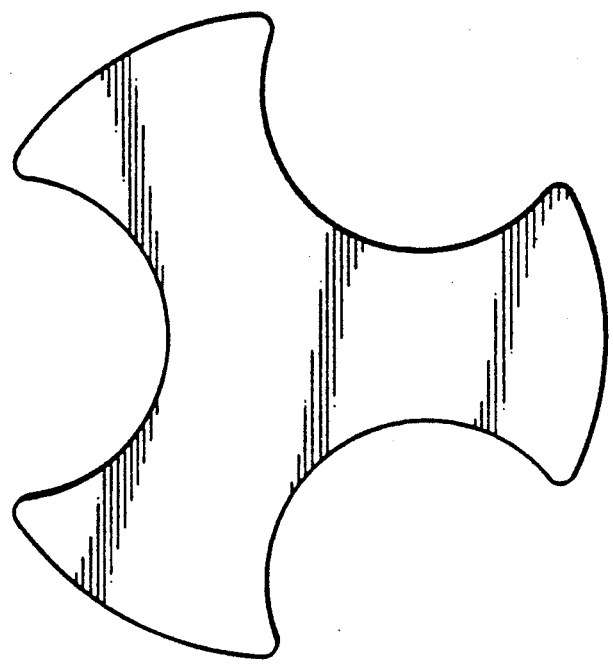
FIG. 1B illustrates, in top elevational view, a solid cylindrical structure with void spaces as equally spaced rounded grooves disposed in the external surface, running substantially vertically from top to bottom.

This invention is directed to shaped oxidation catalyst structures. Accordingly, the primary object of this invention is to provide shaped oxidation catalyst structures containing catalytic material comprised of mixed oxides of vanadium and phosphorus which are suitable for the production of maleic anhydride via the partial oxidation of nonaromatic hydrocarbons in the vapor phase with molecular oxygen or a molecular oxygen-containing gas, the use of which results in enhanced catalyst activity, as determined by weight/weight productivity, when compared to conventional oxidation catalyst shapes for the production of maleic anhydride.

This and other objects, aspects, and advantages of the instant invention will become apparent to those skilled in the art from the accompanying description and claims.

The above objects are achieved by the shaped oxidation catalyst structures of the instant invention which comprise a solid geometric form having at least one (1) void space disposed in the external surface thereof, the shaped structure being characterized by (a) containing catalytic material comprised of mixed oxides of vanadium and phosphorus, and (b) exhibiting (i) a geometric volume of from about 30 percent to about 67 percent of that exhibited by the void space-free solid geometric form, (ii) an external geometric surface area/geometric volume ratio of at least about 20 cm$^{-1}$, (iii) a bulk density of from about 0.4 gram per cubic centimeter (g/cm$^3$) to about 1.4 g/cm$^3$, and (iv) a mechanical resistance sufficient to maintain substantially the structural integrity of the shaped structure under handling and use conditions.

DESCRIPTION OF THE PREFERRED EMBODIMENTS

In accordance with this invention, shaped oxidation catalyst structures are provided for the production of maleic anhydride by the partial oxidation of nonaromatic hydrocarbons in the vapor phase with molecular oxygen or a molecular oxygen-containing gas. The shaped structures comprise a solid geometric form having at least one (1) void space disposed in the external surface thereof. In addition, such shaped structures are characterized by a combination of properties effective to demonstrate enhanced catalyst activity, as determined by weight/weight productivity, when compared to conventional oxidation catalyst shapes for the production of maleic anhydride.

For purposes of this invention, the term "void space" means the unoccupied space in the solid geometric form other than pores and crevices which normally are present in a solid geometric form catalyst structure. The term "weight/weight productivity" means the weight of maleic anhydride (MAN) expressed in grams produced during a single pass of hydrocarbon feedstock over the catalyst per unit of weight of catalyst expressed in kilograms per unit of time expressed in hours, the term expressed as g maleic anhydride/kg catalyst-hour or g MAN/kg cat.-hr. The term "yield" means (a) the ratio of the moles of maleic anhydride obtained to the moles of hydrocarbon feedstock introduced into the reactor multiplied by 100, the term expressed as mol %, and (b) the ratio of the weight of maleic anhydride obtained to the weight of hydrocarbon feedstock introduced into the reactor multiplied by 100, the term expressed as weight % or wt %. The term "selectivity" means the ratio of moles of maleic anhydride obtained to the moles of hydrocarbon reacted or converted multiplied by 100, the term expressed as mol %. The term "conversion" means the ratio of moles of hydrocarbon feedstock reacted to the moles of hydrocarbon introduced into the reactor multiplied by 100, the term expressed as mol %. The term "space velocity" or "gas hourly space velocity" or "GHSV" means the hourly volume of gaseous feed expressed in cubic centimeters (cm$^3$) at 20° C. and atmospheric pressure, divided by the catalyst bulk volume, expressed as cm$^3$/cm$^3$/hour or hr$^{-1}$.

The solid geometric forms suitable to represent base structures of the shaped oxidation catalyst structures of the instant invention include any solid geometric form in which void spaces can be disposed in the external surface thereof to provide the shaped oxidation catalyst structures of the instant invention. Nonlimiting exemplary solid geometric forms include cylinders, cubes, cones, truncated cones, pyramids, truncated pyramids, spheres, prisms, and the like.

A critical feature of the instant invention is the disposition of void spaces in the external surface of the solid geometric form. Suitable void spaces include grooves, holes, dimples, and the like. The void spaces are in general equally spaced or distributed over the external surface in which such void spaces are located. The number and shape of the void spaces disposed in the external surface of the solid geometric form is not narrowly critical. All that is necessary is that the resultant shaped oxidation catalyst structure exhibits certain characterizing properties as hereinafter discussed. Accordingly, the shape of the corners of the void spaces, as well as any protrusions associated therewith, may be angular or rounded and the number of such void spaces, which must be at least one (1), may be any practical number, taking into consideration the dimensions of the void spaces and the available external geometric surface in which they are disposed. In general, it is preferred to have the shape of the corners rounded.

In connection with the disposition of void spaces in the external surface of the solid geometric form, the geometric volume of the shaped oxidation catalyst structures, of necessity, must be reduced to a value less than that of the void space-free solid geometric form. In accordance with the instant invention, the shaped oxidation catalyst structures of the instant invention must exhibit a geometric volume of from about 30 percent to about 67 percent, preferably from about 40 percent to about 61 percent, of that exhibited by the void space-free geometric form. The retention of such geometric volume, in combination with other characterizing properties of the shaped oxidation catalyst structures of the instant invention, results in such structures exhibiting enhanced catalyst activity, as determined by weight/weight productivity, when compared to conventional oxidation catalyst shapes, including corresponding void space-free solid geometric forms, for the production of maleic anhydride.

The shaped oxidation catalyst structures of the instant invention exhibit a characteristic geometric volume and geometric surface area as a consequence of the cross-sectional shape and dimensions associated therewith. The geometric volume and geometric surface area are readily calculated from appropriate measurements associated with the corresponding perfect geometric forms. The shaped oxidation catalyst structures of the instant invention closely approximate such forms and their geometric surface areas and geometric volumes can be closely estimated from the corresponding geometric models. The (external) geometric surface area/geometric volume ratio advantageously is at least 20 $cm^{-1}$, preferably at least about 27 $cm^{-1}$.

The bulk density of the shaped oxidation catalyst structures is indicative of the amount or quantity of catalyst material contained in a specified catalyst shape. It will be apparent, of course, for a shaped structure having specified dimensions, the greater the amount of catalyst material (or material in general, regardless of whether the material is catalyst material or a combination of catalyst material and filler or inert material) contained therein, the greater will be the bulk density. On the other hand, with everything else being equal, the greater the bulk density, the more tightly packed is the material contained therein. This, in turn, is accompanied by a decrease in porosity, thereby inhibiting the movement of reactant gas molecules into and out of the shaped catalyst structure. The shaped oxidation catalyst structures of the instant invention, however, do not suffer from this difficulty in that such structures exhibit a bulk density of from about 0.4 $g/cm^3$ to about 1.4 $g/cm^3$, preferably from about 0.5 $g/cm^3$ to about 1.1 $g/cm^3$.

It will be apparent to those skilled in the art that the shaped oxidation catalyst structures must possess sufficient mechanical resistance or physical strength to withstand handling, transportation from the source of manufacture to the reactor in which it is to be used, and charging into the reactor. In addition, the shaped structures must be able to support their own weight in the reactor. Or stated differently, the shaped oxidation catalyst structures must possess mechanical resistance sufficient to maintain substantially the structural integrity of the shaped structure under handling and use conditions. If the shaped structures has insufficient mechanical resistance, crushing of the shaped structure can result. This, in turn, results in adverse economic consequences such as increased pressure drop and decreased reactant gas flow rates, increased costs for production of the shaped oxidation catalyst structures due to yield losses to fines and broken pieces, and less efficient reactor operation due to hot spots in the catalyst bed. In general, sufficient mechanical resistance, as determined by side crush strength measurements—the amount of pressure required to break or crush the shaped structure—exists for structures exhibiting a side crush strength of from about 4.45 newtons (N) to about 222.4 N (about 1 lb to about 50 lb), preferably from about 13.3 N to about 89 N (3 lb to about 20 lb). Or stated differently, the mechanical resistance of the shaped structure is sufficient to maintain substantially the structural integrity thereof, while at the same time is not excessive to the point that the porosity of the shaped structure is reduced to a value such that the movement of reactant gas molecules into and out of the shaped structure is inhibited.

The shaped oxidation catalyst structures of the instant invention may have any practical size and dimensions, taking into account the overall dimensions of the particular reactor tube in which they are to be used. In general, a base width (that is, the widest portion of the structure) of from about 3.175 mm to about 6.35 mm and a height-to-base width ratio of from about 0.5 to about 2.0 are advantageously employed.

Catalyst materials suitable for use in the instant invention are those known to the art, and in general are materials capable of catalyzing the vapor phase partial oxidation of hydrocarbons to maleic anhydride under oxidation conditions. Such materials in general comprise a vanadium phosphorus oxide complex, optionally further comprising a promoter element. A convenient, albeit nonlimiting, representation of an empirical formula for suitable catalytic material may be expressed as $VP_xO_yM_z$ wherein M is at least one promoter element selected from the group consisting of elements from Groups IA, IB, IIA, IIB, IIIA, IIIB, IVA, IVB, VA, VB, VIB, and VIIIB of the Periodic Table of the Elements, x is a number from about 0.5 to about 2.0, preferably from about 0.95 to about 1.35, y is a number taken to satisfy the valences of V, P, and M in the oxidation states in which they exist in the composition, and z is a number from zero (0) to about 1.0, preferably up to about 0.5.

The term "Periodic Table of the Elements", as employed herein, refers to the Periodic Table of the Elements published in *The Merck Index*, 10th ed., Windholtz, Ed., Merck & Co., Inc., Rahway, N.J., 1983, Inside Front Cover.

Specific, albeit nonlimiting, examples of suitable catalyst materials are those described in several of the references previously noted in the "Description of the Prior Art"—U.S. Pat. Nos. 4,632,915; 4,562,268; 4,333,853; 4,315,864; 4,312,787; 4,251,390; 4,187,235; 4,018,709; 3,980,585; 3,888,866; 3,864,280; 3,862,146; and 3,856,824; and European Patent Application No. 98,039—it being understood, however, that the same are not to be construed as limiting but instead are for purposes of illustration and guidance in the practice of the instant invention. These references are herein incorporated by reference. Among such catalyst materials, those in general preferred for use in the instant invention are those described in U.S. Pat. Nos. 4,632,915 and 4,562,268.

The shaped oxidation catalyst structures of the instant invention may be prepared by blending the catalyst material with shaped structure forming aids known to the art such as graphite or stearic acid and any desirable inert filler material and pressing or compacting in a mold (tableting press equipped with an appropriate die and punch) or by extrusion or casting in accordance with procedures known in the art. In general, the compaction technique is preferred in that shaped structures exhibiting characterizing properties in accordance with the instant invention are more readily obtained. In a similar manner, the absence of the employment of inert filler material is preferred in that the partial oxidation reaction of hydrocarbon to maleic anhydride is advantageously carried out in a manner which maximizes the amount of active catalyst material contained in the specified volume of the reactor to thereby maximize the amount of hydrocarbon converted in a single reactor pass.

The shaped oxidation catalyst structures of the instant invention are useful in a variety of reactors to convert nonaromatic hydrocarbons to maleic anhydride. A typically satisfactory reactor is a heat transfer medium-cooled fixed bed tube-type reactor. The details of operation of such reactors are well known to those skilled in the art. The tubes of such reactors can be constructed of iron, stainless steel, carbon steel, nickel, glass, such as Vycor, and the like and can vary in diameter from about 0.635 cm (0.25 in.) to about 3.81 cm (1.50 in.) and the length can vary from about 15.24 cm (6 in.) to about 762 cm (25 ft). The oxidation reaction is highly exothermic and once reaction is underway, in order to maintain the desired reactor temperature, a heat transfer medium is necessary to conduct heat away from the reactor. Suitable heat transfer media are well known to those skilled in the art and, in general, are materials that remain in the liquid state at process temperatures and have a relatively high thermal conductivity. Examples of useful media include various heat transfer oils, molten sulfur, mercury, molten lead, and salts such as nitrates and nitrites of alkali metals, the salts being preferred due to their high boiling points. A particularly preferred heat transfer medium is a eutectic mixture of potassium nitrate, sodium nitrate and sodium nitrite which not only has a desirably high boiling point, but also, a sufficiently low freezing point that it remains in a liquid state even during periods of reactor shutdown. An additional method of temperature control is to use a metal block reactor whereby the metal surrounding the reaction zone of the reactor acts as a temperature regulating body or by conventional heat exchangers.

In general, the reaction to convert nonaromatic hydrocarbons to maleic anhydride using the shaped oxidation catalyst structures of the instant invention involves charging a mixture of a nonaromatic hydrocarbon having at least four (4) carbon atoms in a straight chain (or in a cyclic structure) and a molecular oxygen-containing gas (including molecular oxygen, itself), such as air or molecular oxygen-enriched air, to a heat transfer medium-cooled reactor or reaction zone packed with the shaped oxidation catalyst structures of the instant invention to contact the hydrocarbon/molecular oxygen-containing gas mixture with the catalyst at elevated temperatures. In addition to the hydrocarbon and molecular oxygen, other gases, such as nitrogen or steam, may be present or added to the reactant feedstream. Typically, the hydrocarbon is admixed with the molecular oxygen-containing gas, preferably air, at a concentration of from about 1 mol % to about 10 mol % hydrocarbon and contacted with the catalyst at a gas hourly space velocity (GHSV), or simply space velocity, of from about 100 hr$^{-1}$ up to about 5,000 hr$^{-1}$ and at a temperature of from about 300° C. to about 600° C., preferably from about 1,000 hr$^{-1}$ to about 3,000 hr$^{-1}$ and from about 325° C. to about 500° C. to produce maleic anhydride.

The initial yield of maleic anhydride, however, may be low. And if this is the case, the catalyst, as will occur to those skilled in the art, can be "conditioned" by contacting the shaped oxidation catalyst structures of the instant invention with low concentrations of hydrocarbon and molecular oxygen-containing gas at low space velocities for a period of time before production operations begin.

Pressure is not critical in the reaction to convert nonaromatic hydrocarbons to maleic anhydride. The reaction may be conducted at atmospheric, superatmospheric, or subatmospheric pressure. It generally will be preferred, however, for practical reasons, to conduct the reaction at or near atmospheric pressure. Typically, pressures of from about $1.013 \times 10^2$ kilopascals-gauge (kPa-g, 14.7 psig. 1 atm) to about $3.45 \times 10^2$ kPa-g (50.0 psig), preferably from about $1.24 \times 10^2$ kPa-g (18.0 psig) to about $2.068 \times 10^2$ kPa-g (30.0 psig), may be conveniently employed.

Maleic anhydride produced by using the shaped oxidation catalyst structures of the instant invention can be recovered by any means known to those skilled in the art. For example, maleic anhydride can be recovered by direct condensation or by absorption in suitable media with subsequent separation and purification of the maleic anhydride.

For purposes of comparing the efficiency, as determined by weight/weight productivity and maximum reaction yield, of the shaped oxidation catalyst structures of the instant invention with oxidation catalyst structures not within the scope of the instant invention, the weight/weight productivity and maximum reaction yield values are determined by carrying out the maleic anhydride production at standardized conditions. And although any standardized set of conditions can be employed to establish weight/weight productivity and maximum reaction yield values, the values reported herein were determined at a hydrocarbon-in-air concentration of 1.5 mol % and 2,000 hr$^{-1}$ while adjusting the hydrocarbon conversion to a value, typically from about 70 mol % to about 90 mol %, sufficient to provide the highest possible yield of maleic anhydride. It will be recognized, of course, that while weight/weight productivity and maximum reaction yield values, as reported herein, are determined at the previously stated standardized conditions, other conditions may be employed, if desired. However, weight/weight productivity and maximum reaction yield values determined at conditions other than 1.5 mol % hydrocarbon-in-air concentration and 2,000 hr$^{-1}$ space velocity while adjusting the hydrocarbon conversion to a value sufficient to provide the highest possible yield of maleic anhydride generally will differ from those determined at the standardized conditions employed herein. As a result, direct comparison of weight/weight productivity and maximum reaction values for different catalyst structures may be made only if such values are determined under the same standardized conditions.

A large number of nonaromatic hydrocarbons having from four to 10 carbon atoms can be converted to maleic anhydride using the shaped oxidation catalyst structures of the instant invention. It is only necessary that the hydrocarbon contain not less than four carbon atoms in a straight chain or in a cyclic ring. As an example, the saturated hydrocarbon n-butane is satisfactory, but isobutane (2-methylpropane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane, so long as a hydrocarbon chain having at least four carbon atoms in a straight chain is present in the saturated hydrocarbon molecule.

Unsaturated hydrocarbons are also suitable for conversion to maleic anhydride using the shaped oxidation catalyst structures of the instant invention. Suitable unsaturated hydrocarbons include the butenes (1-butene and 2-butene), 1,3-butadiene, the pentenes, the hexenes, the heptenes, the octenes, the nonenes, the decenes, and mixtures of any of these, with or without the butenes, again, so long as the requisite hydrocarbon chain having at least four carbon atoms in a straight chain is present in the molecule.

Cyclic compounds such as cyclopentane and cyclopentene also are satisfactory feed materials for conversion to maleic anhydride using the shaped oxidation catalyst structures of the instant invention.

Of the aforementioned feedstocks, n-butane is the preferred saturated hydrocarbon and the butenes are the preferred unsaturated hydrocarbons, with n-butane being most preferred of all feedstocks.

It will be noted that the aforementioned feedstocks need not necessarily be pure substances, but can be technical grade hydrocarbons.

The principal product from the oxidation of the aforementioned suitable feed materials is maleic anhydride, although small amounts of citraconic anhydride (methyl maleic anhydride) also may be produced when the feedstock is a hydrocarbon containing more than four carbon atoms.

The following specific examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLE 1

A twelve-liter, round bottom flask, fitted with a paddle stirrer, a thermometer, a heating mantle, and a reflux condenser, was charged with 9,000 mL of isobutyl alcohol, 378.3 g (4.20 mol) of oxalic acid ($C_2H_2O_4$), and 848.4 g (4.66 mol) of vanadium pentoxide ($V_2O_5$). To this stirred mixture was added 997.6 g (10.76 mol) of phosphoric acid ($H_3PO_4$, 105.7% by weight). The resultant mixture was refluxed for about 16 hours to give a bright blue mixture. After stripping off 6 L of isobutyl alcohol over a 3-hour period, the mixture was cooled and quantitatively transferred to a flat porcelain dish and dried for 48 hours at 110° C. in nitrogen, followed by 48 hours at 150° C. in air. The dried material was transferred to another box oven and heated in air at 250°–260° C. for approximately one hour to yield a grey-black catalyst precursor powder.

The catalyst precursor powder was blended to contain approximately four (4.0) weight % graphite and compressed on a Stokes 512 Rotary Tableting machine equipped with appropriate dies and punches to produce the desired shaped catalyst structure, 1.27 cm cylinders with a tablet density of 1.30–1.50 g/cm$^3$. The 1.27 cm slugs were ground to produce a tablet feed powder in the size range of from 18 mesh [U.S. Standard Sieve Size, 1.00 millimeter (mm)] to 30 mesh (600 microns, $\mu$m) and fed into the tableting machine equipped with appropriate dies and punches to produce the shaped catalyst structure of interest. The compaction pressure was adjusted to produce structures with average (side) crush strengths of from 13.3 N to 89 N (3 lb to 20 lb). The characterizing properties of the shaped catalyst structures produced are summarized in Table 1.

Each of the shaped catalyst structures produced was activated. The shaped catalyst structure was placed onto a 30.48 cm $\times$ 30.48 cm $\times$ 2.54 cm tray formed from stainless steel mesh screen having approximately 40% open area. The tray was transferred to an air-purged box oven that previously had been heated to approximately 425° C. This temperature was maintained for a period of time from approximately one hour to about two hours. Thereafter, the tray of shaped catalyst structures was removed from the oven and cooled. The tray of shaped catalyst structures were then transferred to a box oven purged with nitrogen gas and heated to approximately 275° C., at which temperature the atmosphere in the oven was changed to a mixture of approximately 50 % by volume nitrogen and 50 % by volume steam. The temperature was raised over a period of from one hour to two hours to approximately 425° C. and maintained at such temperature for approximately six hours. The tray of shaped catalyst structures was then allowed to cool to room temperature (approximately 25° C.) while purging the oven with dry nitrogen. The shaped catalyst structures were charged to a 2.10 cm inside diameter x 121.9 cm long fixed bed tubular reactor and performance tested as described in Example 5, below.

EXAMPLE 2

This example illustrates the preparation of a vanadium phosphorus oxide in accordance with the procedure described for Examples 1–7 of U.S. Pat. No. 4,333,853.

A twelve-liter, round bottom flask equipped as described in Example 1, above, was charged with 7,340 mL of isobutyl alcohol and 513.5 g (2.82 mol) of $V_2O_5$. Stirring was begun and a solution of 663.97 g (6.78 mol) of 100% $H_3PO_4$ in 1129 mL of isobutyl alcohol. The resultant mixture was then refluxed for about 16 hours to give a light blue mixture. The mixture was cooled and the precipitate was filtered and the precipitate dried at ambient temperatures under vacuum. The dried precipitate thereafter was washed with approximately 1200 mL of isobutyl alcohol, followed by drying at 145° C. for approximately 2.5 hours, and calcining for approximately one hour in air at 400° C.

The catalyst precursor powder was blended to contain approximately 2.54 weight % stearic acid and fed into a Stokes 512 Rotary Tableting machine equipped with appropriate dies and punches to produce the desired shaped catalyst structure. The compaction pressure was adjusted to produce structures with average (side) crush strengths of from 13.3 N to 89 N (3 lb to 20 lb). The characterizing properties of the shaped catalyst structures produced are summarized in Table 1. The thusly prepared shaped catalyst structures were charged to a 2.10 cm inside diameter $\times$ 121.9 cm long (0.83 in. inside diameter $\times$ 4 ft long) fixed bed tubular reactor and performance tested as described in Example 5, below.

EXAMPLE 3

This example illustrates the preparation of a lithium/zinc-promoted vanadium phosphorus oxide catalyst in accordance with the procedure described for Examples 1–7 of U.S. Pat. No. 4,333,853.

A twelve-liter, round bottom flask equipped as described in Example 1, above, except that it was further equipped with a Dean Stark trap and a gas dispersion tube, was charged with 6,500 mL of isobutyl alcohol and 1145.0 g (6.29 mol) of $V_2O_5$. Stirring was begun and dry hydrogen chloride (HCl) was passed into the stirred mixture at a rate sufficient to maintain the reaction temperature at approximately 50° C. After 6 hours and 43 minutes of HCl addition a dark reddish brown solution resulted. To this solution was added a solution containing 1089.5 g (9.51 mol) of 85.5% $H_3PO_4$, 422.0 g (2.97 mol) of phosphorus pentoxide ($P_2O_5$) dissolved in 1500 mL of isobutyl alcohol. An additional 100 mL of isobutyl alcohol was used to rinse the phosphorus-containing solution into the vanadium-containing solution. Zinc chloride ($ZnCl_2$, 17.17 g, 0.13 mol) and 1.07 g (0.025 mol) of lithium chloride (LiCl) were then added to the reaction solution. The resultant solution was heated to reflux and refluxed for approximately two (2) hours, followed by stripping off of 5.33 L of isobutyl alcohol over a period of four (4) hours. The mixture was cooled and quantitatively transferred to a porcelain dish and dried at 150° C.

The catalyst precursor powder was blended to contain approximately four (4.0) weight % graphite and compressed on a Stokes 512 Rotary Tableting machine equipped with appropriate dies and punches to produce the desired shaped catalyst structure, 1.27 cm cylinders with a tablet density of approximately 1.90 g/cm$^3$. The 1.27 cm slugs were ground to produce a tablet feed powder in the size range of from 18 mesh (U.S. Standard Sieve Size, 1.00 mm) to 30 mesh (600 μm) and fed into the tableting machine equipped with appropriate dies and punches to produce the shaped catalyst structure of interest. The compaction pressure was adjusted to produce structures with average (side) crush strengths of from 13.3 N to 89 N (3 lb to 20 lb). The characterizing properties of the shaped catalyst structures produced are summarized in Table 1. The thusly prepared shaped catalyst structures were activated according to the activation procedure described in U.S. Pat. No. 4,333,853 by charging the structures to a 2.10 cm inside diameter×121.9 cm long (0.83 in. inside diameter×4 ft long) fixed bed tubular reactor. The reactor was warmed slowly to 400° C. while passing a gas stream containing 0.5-0.7 mol % n-butane in air over the shaped catalyst structures, beginning at approximately 280° C. After the temperature had reached 400° C., the shaped catalyst structures were aged by continuing to pass the n-butane-in-air stream over the catalyst for approximately 24 hours. The thusly activated and conditioned shaped catalyst structures were performance tested as described in Example 5, below.

EXAMPLE 4

This example illustrates the preparation of an iron/lithium-promoted vanadium phosphorus oxide catalyst in accordance with the procedure described in Example 1 of U.S. Pat. No. 4,632,915.

A twelve-liter, round bottom flask equipped as described in Example 1, above, except that it was further equipped with a Water-cooled Dean Stark trap and a coarse-frit gas dispersion tube, was charged with 8,300 mL of isobutyl alcohol. Stirring was commenced and the isobutyl alcohol was cooled to a temperature of from about 10° C. to about 15° C. To the cooled isobutyl alcohol was added a solution of 901.8 g (7.87 mol) of 85.5% $H_3PO_4$ and 343.4 g (2.42 mol) of $P_2O_5$ maintained at room temperature. The resultant solution was cooled to a temperature of from 5° C. to about 10° C. To this cooled solution was added, with stirring, 963.0 g (5.29 mol) of $V_2O_5$, 1.35 g (0.032 mol) of LiCl, 0.96 g (0.017 mol or g-atom) of iron powder, and an additional 1.0 L of isobutyl alcohol. Anhydrous HCl (2037.0 g, 55.81 mol) gas was added via the gas dispersion tube to the stirred reaction mixture over a 4.67-hour period while maintaining the temperature between 40° C. and 50° C. The solution was heated to reflux and maintained at reflux for approximately two (2) hours. Thereafter, 5.4 L of distillate was removed at atmospheric pressure over a period of five (5) hours, followed by an additional 1.38-hour period of reflux, followed by removal of an additional 1.5 L of distillate over a 2.36-hour period. The mixture was cooled and quantitatively transferred to a porcelain dish and dried in a box oven at 150° C. for approximately 5.5 hours. The dried material was then transferred to another box oven and heated in nitrogen at a temperature between 250° C. and 260° C. for approximately three (3) hours, followed by gradual replacement of the nitrogen atmosphere by air and heating an additional three (3) hours to yield a grey-black catalyst precursor powder.

The catalyst precursor powder was blended to contain approximately four (4.0) weight % graphite and compressed on a Stokes 512 Rotary Tableting machine equipped with appropriate dies and punches to produce the desired shaped catalyst structure, 1.27 cm cylinders with a tablet density of approximately 1.90 g/cm$^3$. The 1.27 cm slugs were ground to produce a tablet feed powder in the size range of from 18 mesh (U.S. Standard Sieve Size, 1.00 mm) to 30 mesh (600 μm) and fed into the tableting machine equipped with appropriate dies and punches to produce the shaped catalyst structure of interest. The compaction pressure was adjusted to produce structures with average (side) crush strengths of from 13.3 N to 89 N (3 lb to 20 lb). The characterizing properties of the shaped catalyst structures produced are summarized in Table 1. The thusly prepared shaped catalyst (precursor) structures were activated according to the activation procedure described in U.S. Pat. No. 4,632,915, except that the structures were charged to a 2.10 cm inside diameter×121.9 cm long (0.83 in. inside diameter×4 ft long) fixed bed tubular reactor. Following the activation, the shaped catalyst structures were conditioned by warming the reactor at 1° C. per hour to 400° C. while passing a gas stream containing 0.6 mol % n-butane in air over the shaped catalyst structures, beginning at approximately 280° C. After the temperature had reached 400° C., the shaped catalyst structures were aged by continuing to pass the n-butane-in-air stream over the catalyst for approximately 24 hours. The thusly activated and conditioned shaped catalyst structures were performance tested as described in Example 5, below.

TABLE 1

| Ex. No. | Composition Empirical Form. | Type | Void Space. No. | Size, mm Height | Size, mm Width | Side Crush Stren.[1], N | Side Crush Vol. Rat.[2], % | Surface/ Vol.[3], cm$^{-1}$ | Bulk Dens.[4], g/cm$^3$ |
|---|---|---|---|---|---|---|---|---|---|
| 1A[5] | $VP_{1.15}O_x$ | Cylinder | None | 3.73 | 3.18 | 66.75 | 100.0 | 18.0 | 0.84 |
| 1B[5] | " | " | Centered Core Hole[6, 7] | 4.76 | 4.76 | 35.60 | 89.0 | 17.0 | 0.87 |
| 1C | " | " | Grooves[8], 6 | 5.36 | 5.56 | 48.95 | 67.0 | 20.0 | 0.66 |

TABLE 1-continued

| Ex. No. | Composition Empirical Form. | Type | Void Space. No. | Size, mm Height | Size, mm Width | Side Crush Stren.[1], N | Vol. Rat.[2], % | Surface/ Vol.[3], cm$^{-1}$ | Bulk Dens.[4], g/cm$^3$ |
|---|---|---|---|---|---|---|---|---|---|
| 1D | " | " | Grooves[9], 3 | 3.97 | 3.97 | 35.60 | 61.0 | 27.0 | 0.64 |
| 1E | " | " | Grooves[10], 3 | 5.56 | 5.56 | 35.60 | 45.0 | 20.0 | 0.66 |
| 2A[5] | $VP_{1.2}O_x$ | " | None | 5.47 | 4.76 | 31.15 | 100.0 | 13.0 | 0.83 |
| 2B[5] | " | " | Centered Core Hole[6, 7] | 4.76 | 4.76 | 35.60 | 89.0 | 17.0 | 0.96 |
| 2C | " | " | Grooves[9], 3 | 3.97 | 3.97 | 35.60 | 61.0 | 27.0 | 0.65 |
| 3A[5] | $VZn_{0.01}Li_{0.002}P_{1.2}O_x$ | " | Centered Core Hole[6, 7] | 4.29 | 4.76 | 31.15 | 89.0 | 17.0 | 1.09 |
| 3B | " | " | Grooves[9], 3 | 3.97 | 3.97 | 35.60 | 61.0 | 27.0 | 0.87 |
| 4A[5] | $VFe_{0.0016}Li_{0.003}P_{1.2}O_x$ | " | Centered Core Hole[6, 7] | 4.14 | 4.76 | 35.60 | 89.0 | 17.0 | 1.05 |
| 4B | " | " | Grooves[9], 3 | 3.97 | 3.97 | 31.15 | 61.0 | 27.0 | 0.87 |

Figure 1A:
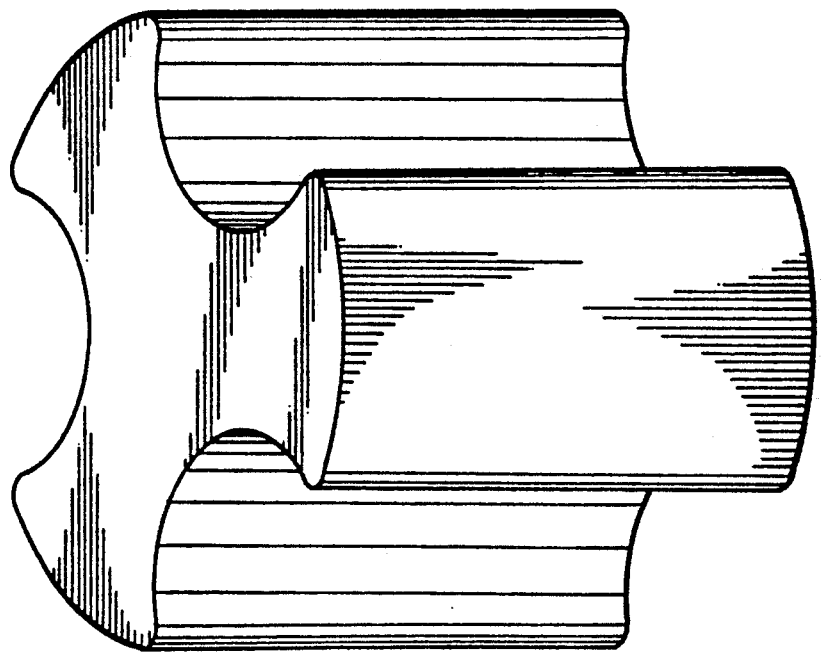
FIG. 1A illustrates a solid cylindrical structure with void spaces as equally spaced rounded grooves disposed in the external surface, running substantially vertically from top to bottom.
Figure 2B:
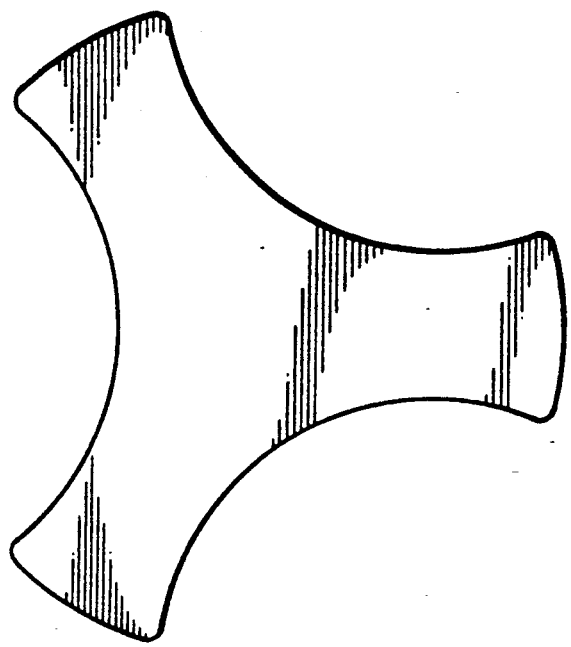
FIG. 2B illustrates, in top elevational view, a variation of the structure illustrated in FIG. 1B with void spaces as equally spaced rounded grooves disposed in the external surface, running substantially vertically from top to bottom.
Figure 2A:
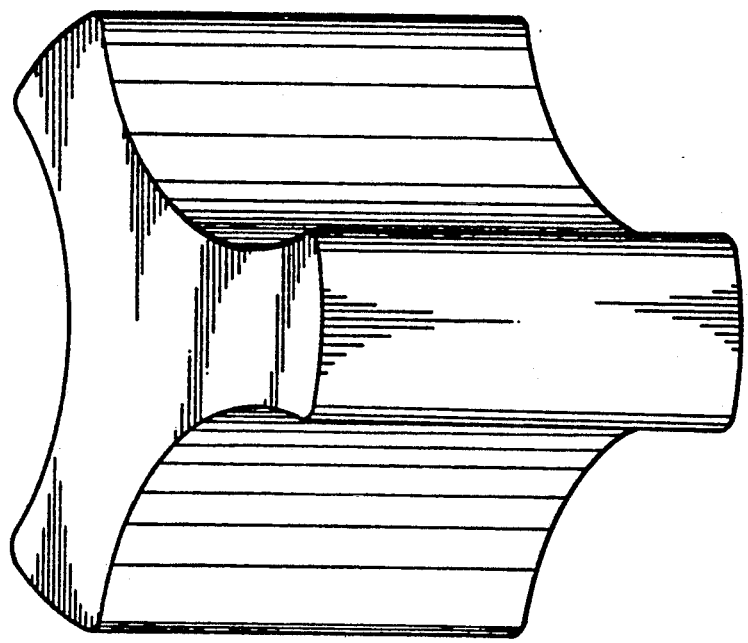
FIG. 2A illustrates a variation of the structure illustrated in FIG. 1A with void spaces as equally spaced rounded grooves disposed in the external surface, running substantially vertically from top to bottom.
Figure 3B:
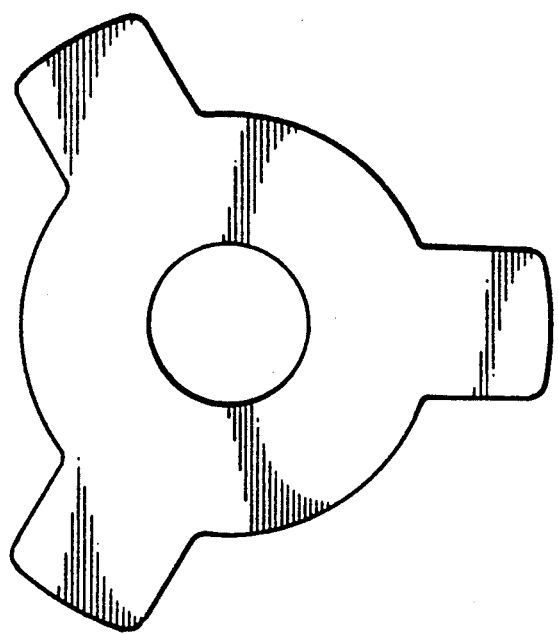
FIG. 3B illustrates, in top elevational view, a solid cylindrical structure with void spaces as equally spaced rounded grooves disposed in the external surface and a centrally located bore.
Figure 3A:
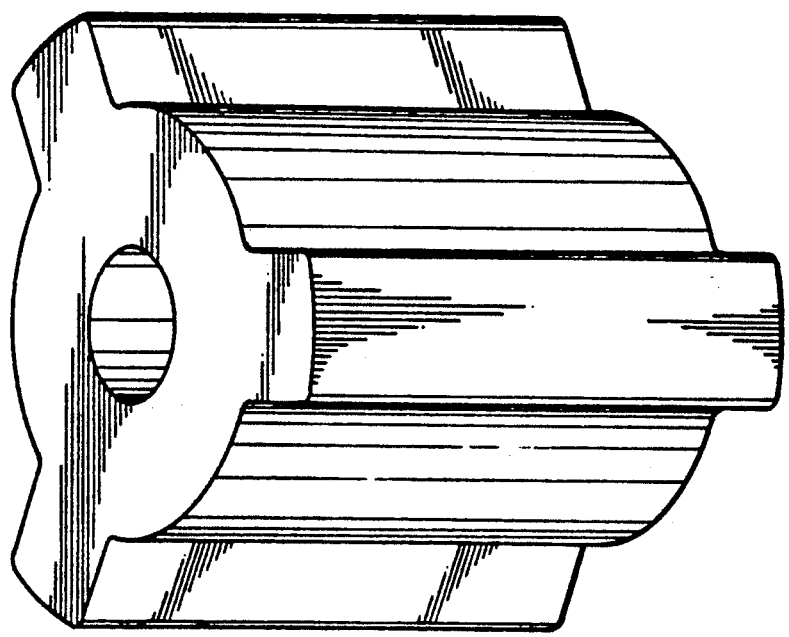
FIG. 3A illustrates a solid cylindrical structure with void spaces as equally spaced rounded grooves disposed in the external surface and a centrally located bore.
Figure 5A:
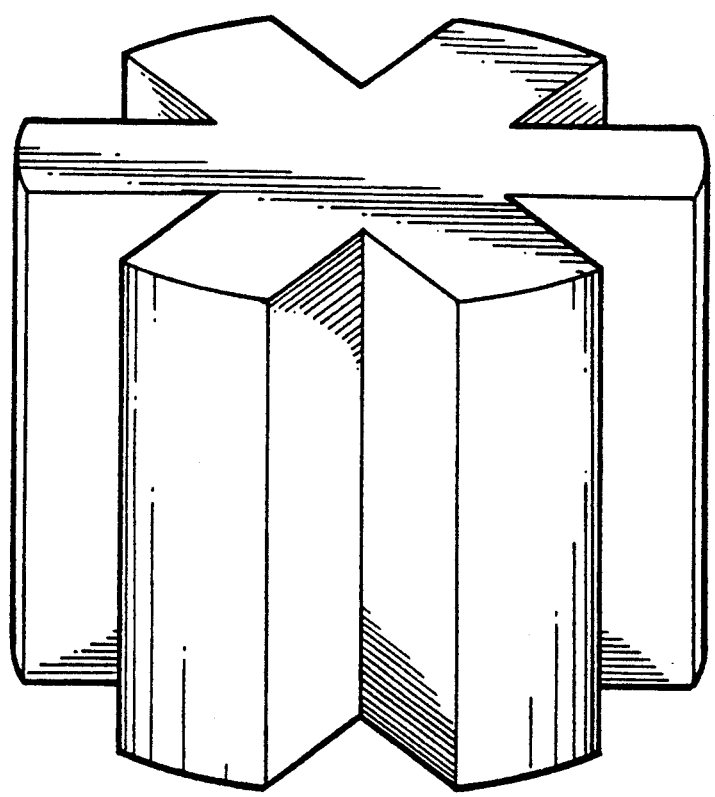
FIG. 5A illustrates a solid cylindrical structure with void spaces as equally spaced angular grooves disposed in the external surface, running substantially vertically from top to bottom.
Figure 5B:
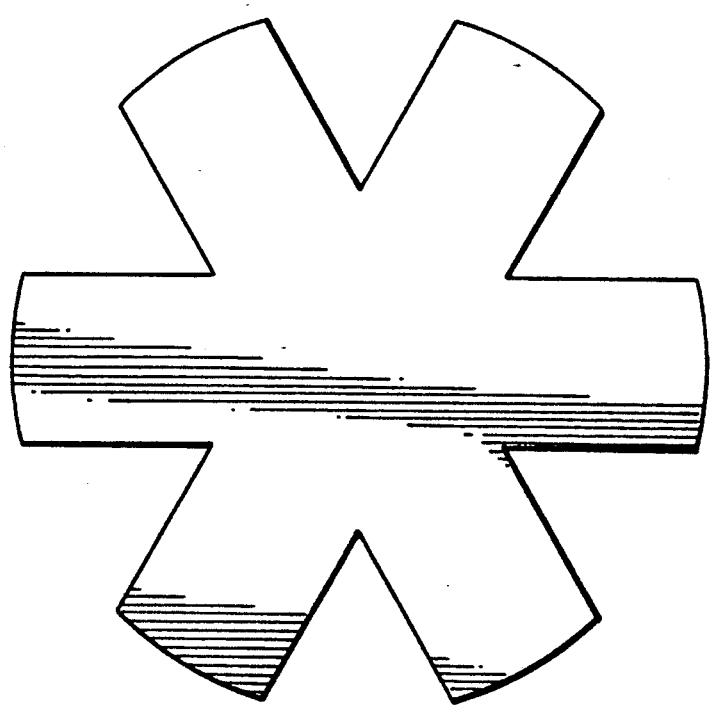
FIG. 5B illustrates, in top elevational view, a solid cylindrical structure with void spaces as equally spaced angular grooves disposed in the external surface, running substantially vertically from top to bottom.
Figure 6A:
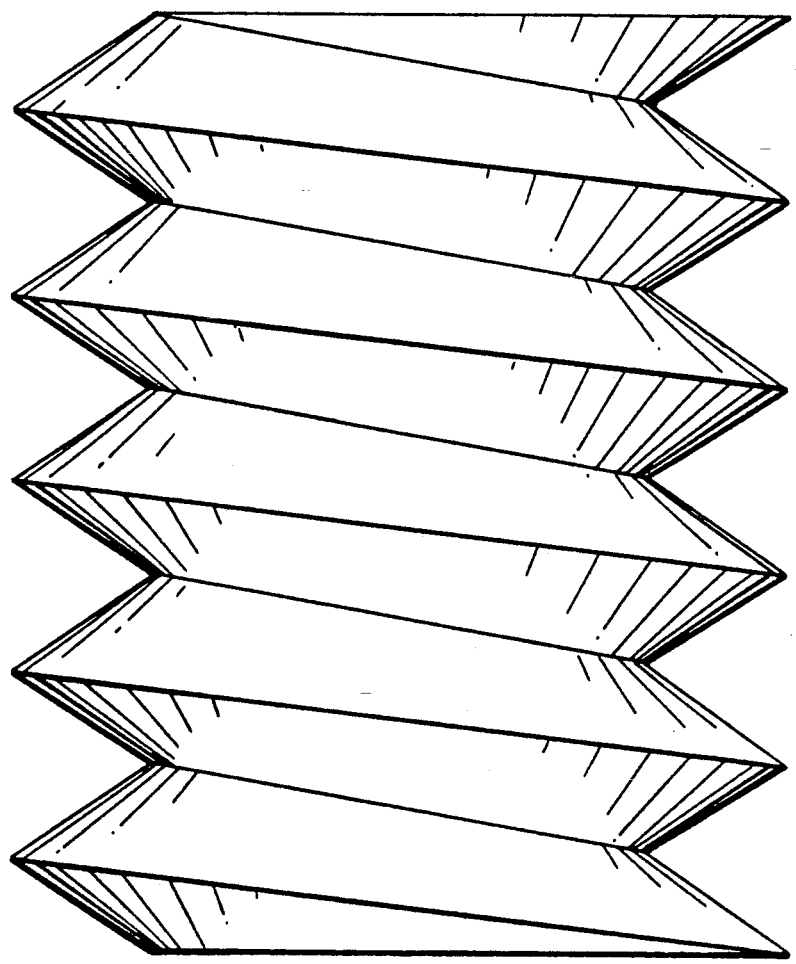
FIG. 6A illustrates a solid cylindrical structure with a void space as a continuous angular spiral disposed in the external surface running from top to bottom.
Figure 6B:
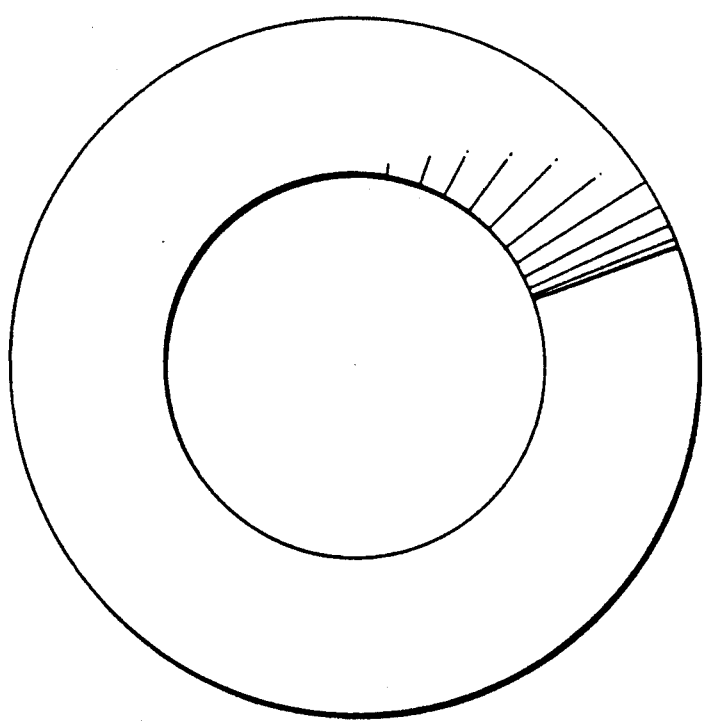
FIG. 6B illustrates, in top elevational view, a solid cylindrical structure with a void space as a continuous angular spiral disposed in the external surface running from top to bottom.
Figure 7B:
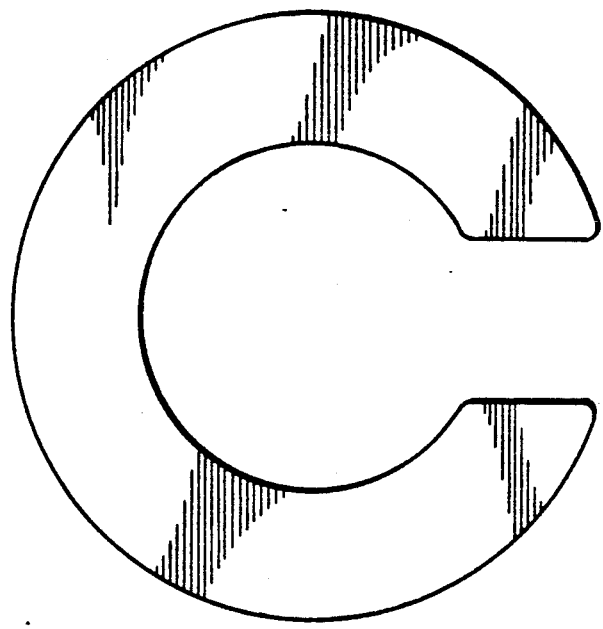
FIG. 7B illustrates, in top elevational view, a solid cylindrical structure with a void space as a rounded groove disposed in the external surface in communication with a centrally located bore.
Figure 7A:
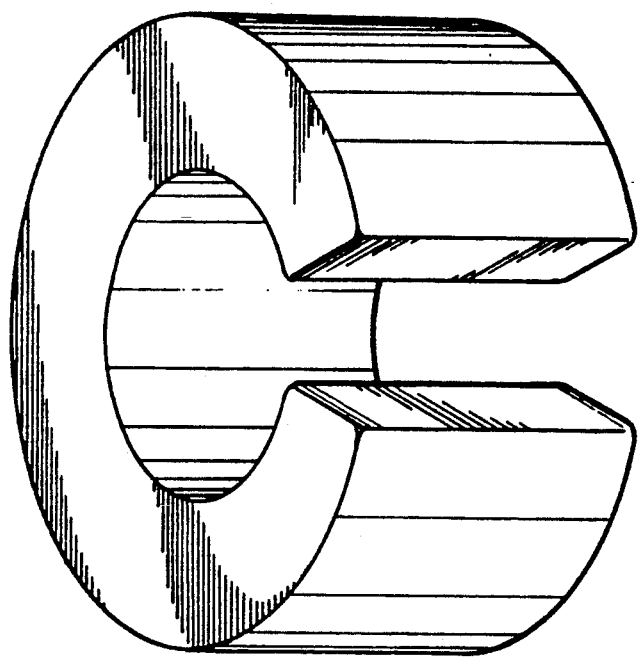
FIG. 7A illustrates a solid cylindrical structure with a void space as a rounded groove disposed in the external surface in communication with a centrally located bore.
Figure 8B:
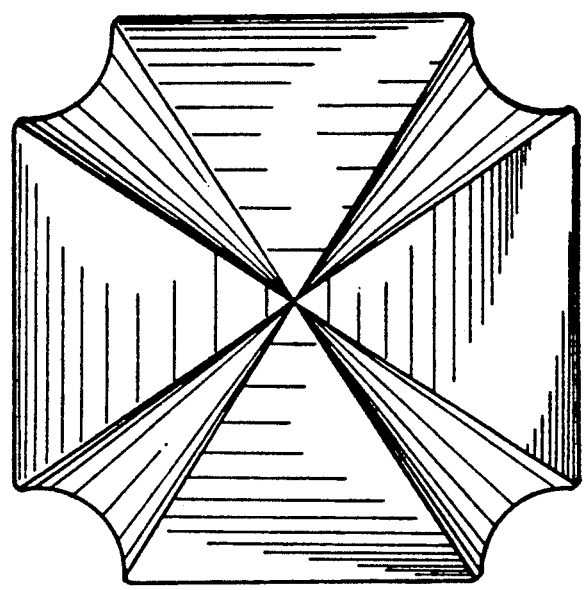
FIG. 8B illustrates, in top elevational view, a solid square-based pyramidal structure with void spaces as equally spaced rounded grooves disposed in the external surface at the corner edges.
Figure 8A:
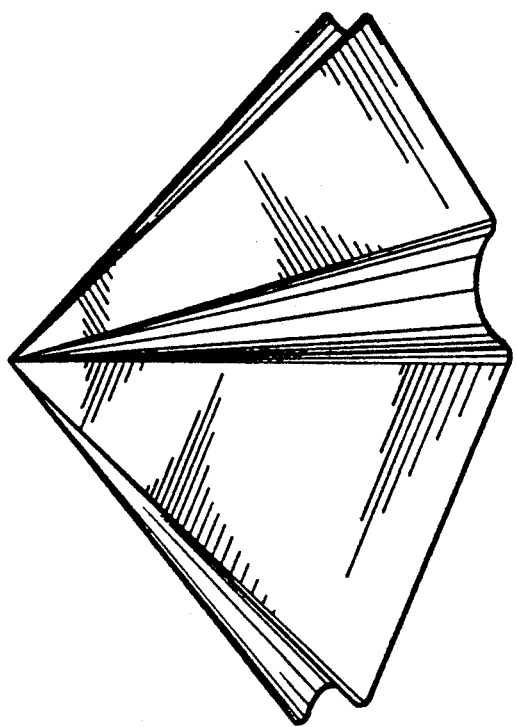
FIG. 8A illustrates a solid square-based pyramidal structure with void spaces as equally spaced rounded grooves disposed in the external surface at the corner edges.
Figure 9B:
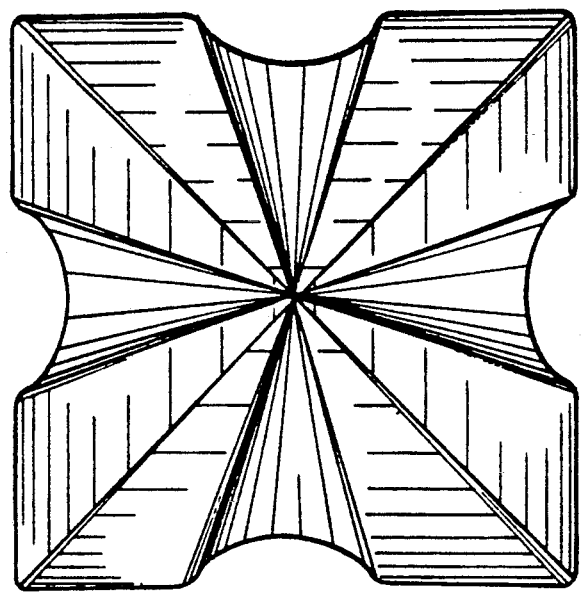
FIG. 9B illustrates, in top elevational view, a solid square-based pyramidal structure with void spaces as equally spaced rounded grooves disposed in the external surface at the sides, running along the sloping sides from top to bottom.
Figure 9A:
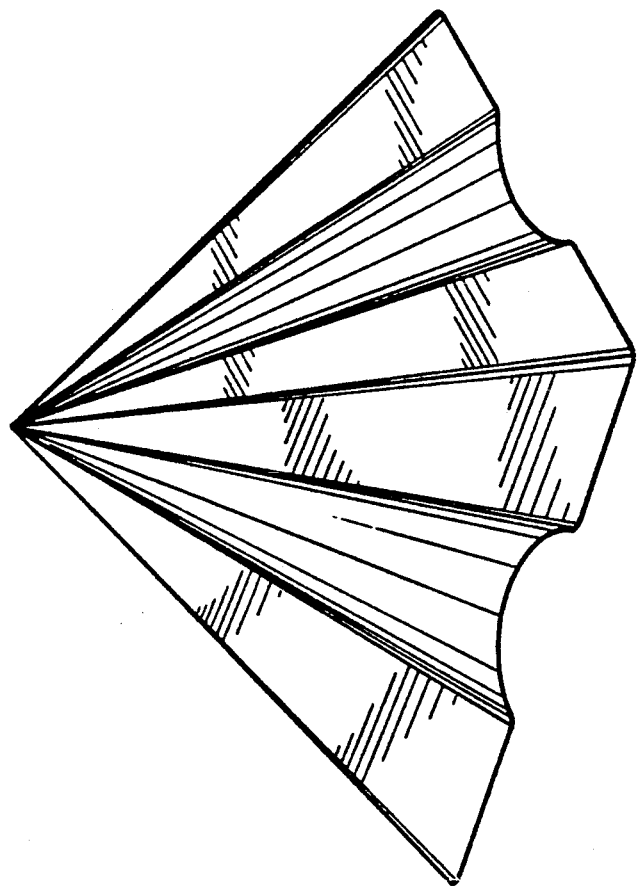
FIG. 9A illustrates a solid square-based pyramidal structure with void spaces as equally spaced rounded grooves disposed in the external surface at the sides, running along the sloping sides from top to bottom.
Figure 10A:
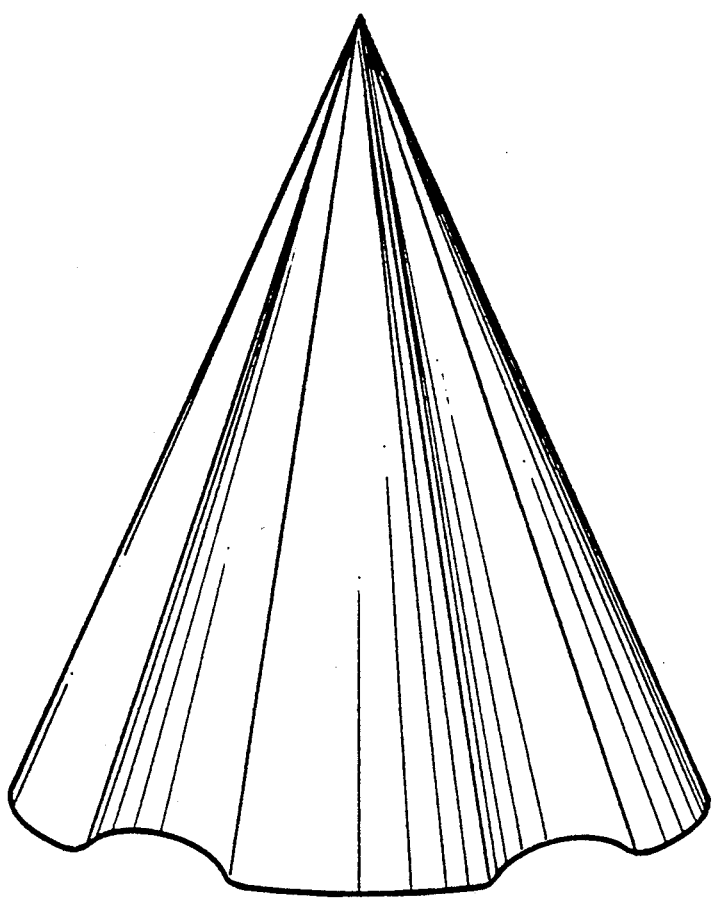
FIG. 10A illustrates a solid conical structure with void spaces as equally spaced rounded grooves disposed in the external surface, running along the sloping sides from top to bottom.
Figure 10B:
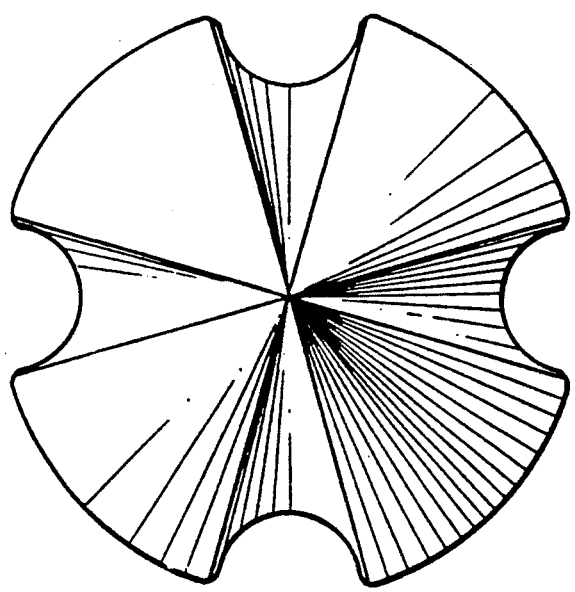
FIG. 10B illustrates, in top elevational view, a solid conical structure with void spaces as equally spaced rounded grooves disposed in the external surface, running along the sloping sides from top to bottom.
Figure 11A:
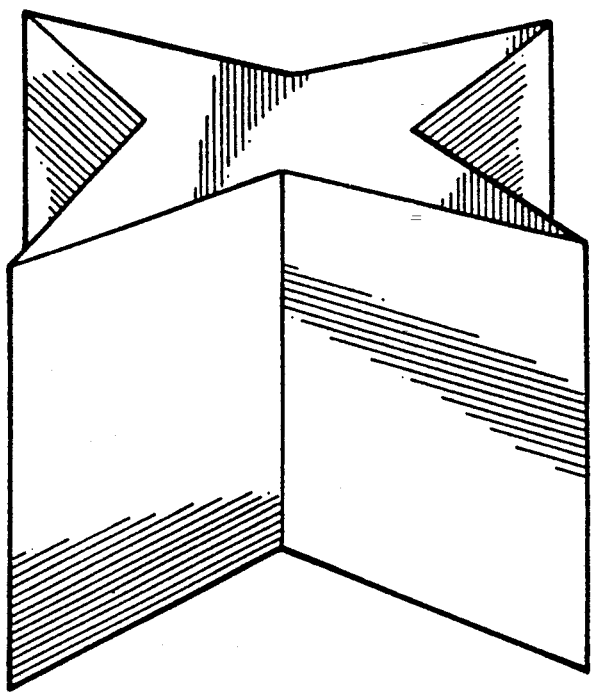
FIG. 11A illustrates a solid cubical structure with void spaces as equally spaced angular grooves disposed in the external surface at the sides, running substantially vertically from top to bottom.
Figure 11B:
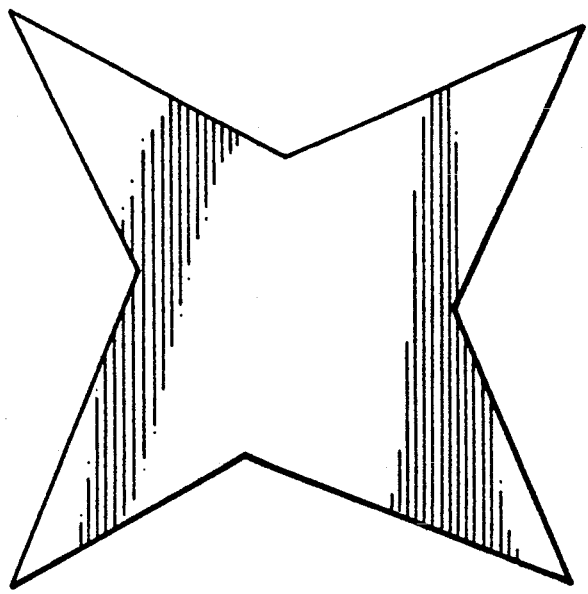
FIG. 11B illustrates, in top elevational view, a solid cubical structure with void spaces as equally spaced angular grooves disposed in the external surface at the sides, running substantially vertically from top to bottom.
Figure 12A:
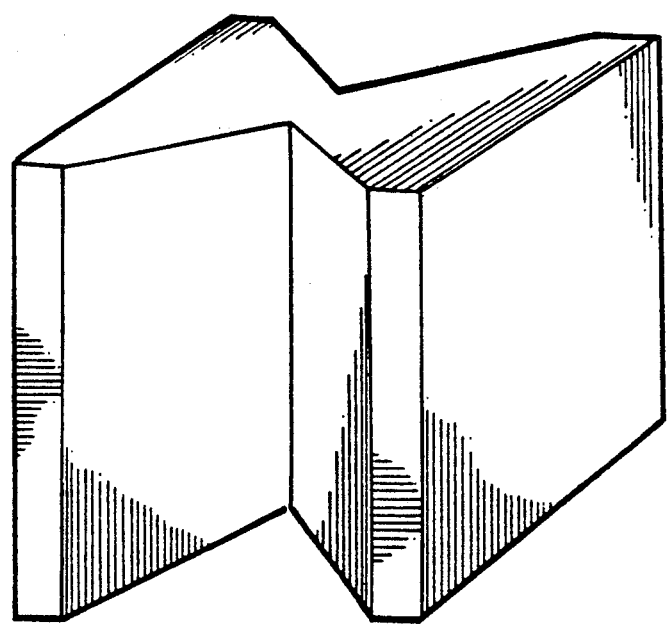
FIG. 12A illustrates a solid cubical structure with void spaces as equally spaced angular grooves disposed in the external surface at the sides, running substantially vertically from top to bottom.
Figure 12B:
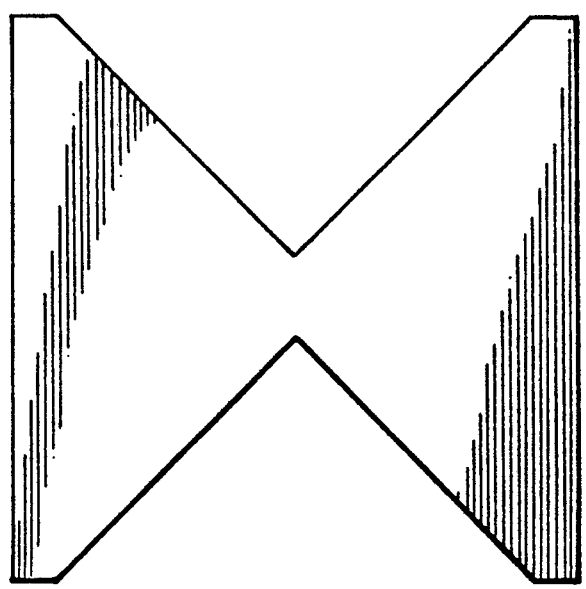
FIG. 12B illustrates, in top elevational view, a solid cubical structure with void spaces as equally spaced angular grooves disposed in the external surface at the sides, running substantially vertically from top to bottom.
Figure 13A:
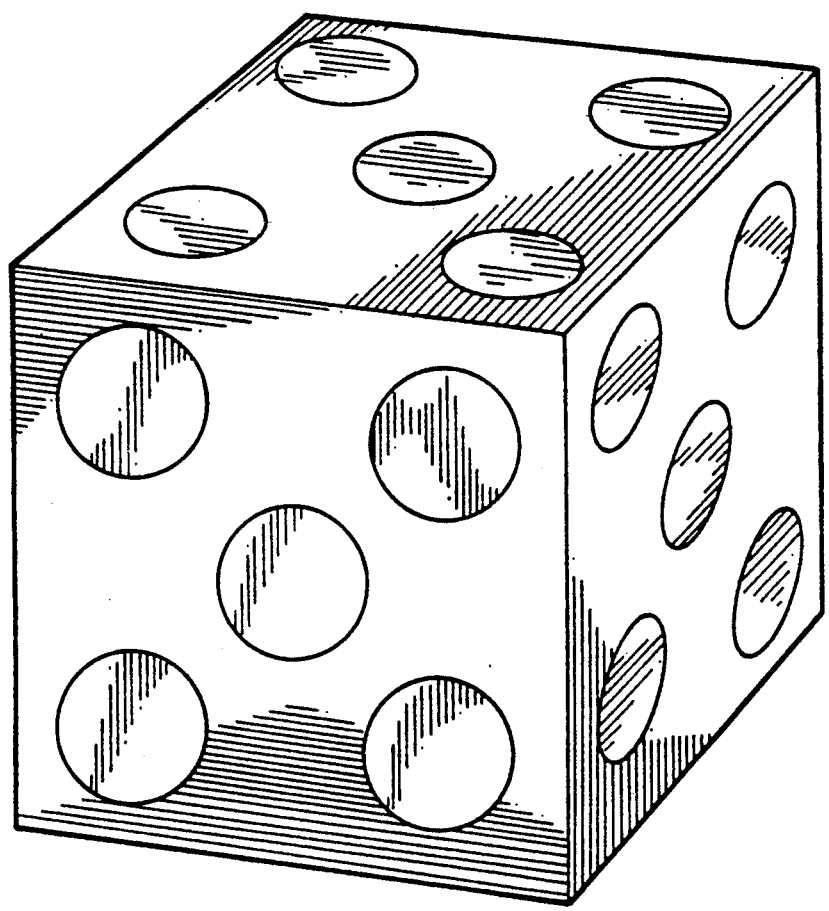
FIG. 13A illustrates a solid cubical structure with void spaces as equally spaced rounded dimples disposed in the external surface at the sides, top, and bottom.
Figure 13B:
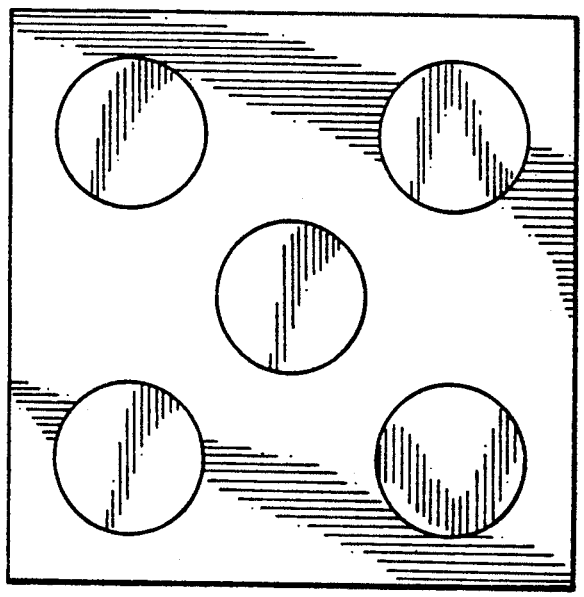
FIG. 13B illustrates, in top elevational view, a solid cubical structure with void spaces as equally spaced rounded dimples disposed in the external surface at the sides, top, and bottom.
Figure 14A:
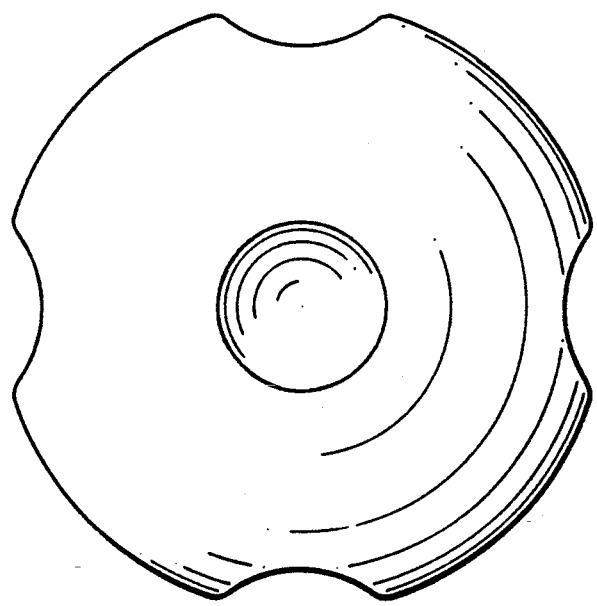
FIG. 14A illustrates a solid spherical structure with void spaces as equally spaced rounded dimples disposed in the external surface.
Figure 14B:
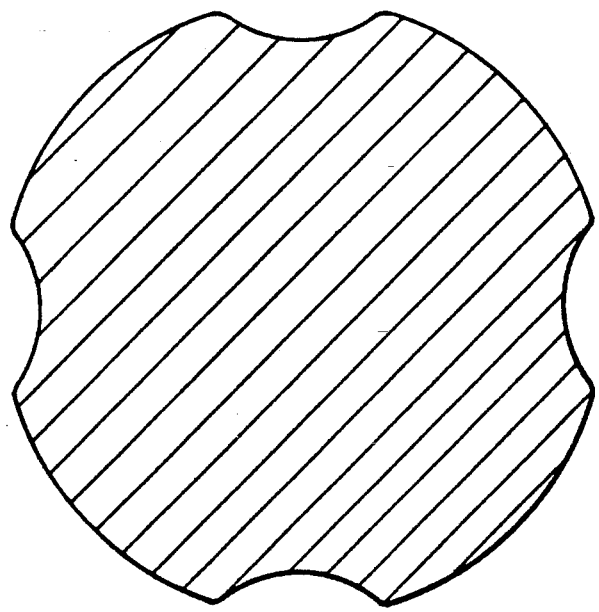
FIG. 14B illustrates, in cross sectional view at the equator, a solid spherical structure with void spaces as equally spaced rounded dimples disposed in the external surface.

[1] Average of at least 10 crush determinations.
[2] (Geometric Volume of Shaped Structure/Geometric Volume of Solid Geometric Form) × 100.
[3] External Surface Area of Shaped Structures, cm$^2$/Geometric Volume of Shaped Structure, m$^3$.
[4] Determined by accurately weighing a given volume of settled shaped structures.
[5] Comparative example.
[6] 1.58 mm diameter centered core hole.
[7] See FIG. 4A and 4B.
[8] See FIG. 5A and 5B.
[9] See FIG. 1A and 1B.
[10] See FIG. 2A and 2B.

EXAMPLE 5

Each shaped catalyst structure type was performance tested at a standardized set of reactor conditions—1.5 mol % n-butane, 1.034×10$^2$ kPa-g (15.0 psig) inlet pressure, and 2,000 GHSV. The shaped catalyst structure of interest was charged to a 2.10 cm inside diameter×121.9 cm long (0.827 in. inside diameter×4 ft long) reactor to its usable height of 121.9 cm. In so doing, the amount of catalyst charged to the reactor was a direct result of the tube filling characteristics of the shaped catalyst structure of interest. The catalyst was run for at least 200 hours at the standardized performance test conditions prior to carrying out yield optimization. The maximum yield was determined for each structure type by raising the n-butane conversion until no further increase in reaction yield was observed. The parameters and results are tabulated in Table 2.

TABLE 2

| Ex. No. | OST[1], hr | Catalyst Rx Char.[2], kg | Catalyst Rx Char. Dens.[3], kg/m$^3$ × 10$^2$ | Temp. °C. Bath | Temp. °C. Hot Spot | Conv. mol % | Yield mol % | Yield wt % | Wt/Wt Prod. g MAN/ kg cat-hr |
|---|---|---|---|---|---|---|---|---|---|
| 1A[4] | 3,679 | 0.336 | 7.96 | 410 | 465 | 74.0 | 51.0 | 86.2 | 77.7 |
| 1B[4] | 1,657 | 0.303 | 7.18 | 439 | 490 | 79.0 | 50.0 | 84.5 | 84.5 |
| 1C | 536 | 0.241 | 5.71 | 424 | 471 | 77.3 | 50.0 | 84.5 | 106.2 |
| 1D | 1,500 | 0.253 | 5.99 | 421 | 474 | 80.0 | 53.0 | 89.6 | 107.3 |
| 1E | 1,042 | 0.261 | 6.18 | 424 | 488 | 78.0 | 51.0 | 86.2 | 100.0 |
| 2A[4] | 647 | 0.311 | 7.37 | 408 | 449 | 76.3 | 49.9 | 84.3 | 82.2 |
| 2B[4] | 1,215 | 0.317 | 7.51 | 408 | 453 | 78.0 | 51.6 | 87.2 | 83.3 |
| 2C | 815 | 0.276 | 6.54 | 405 | 455 | 78.1 | 53.0 | 89.6 | 98.3 |
| 3A[4] | 1,405 | 0.391 | 9.27 | 433 | 472 | 76.8 | 47.1 | 79.6 | 61.7 |
| 3B | 794 | 0.335 | 7.94 | 433 | 486 | 76.0 | 49.0 | 82.8 | 74.9 |
| 4A[4] | 1,245 | 0.427 | 10.12 | 418 | 439 | 75.0 | 51.5 | 87.0 | 61.8 |
| 4B | 1,210 | 0.339 | 8.033 | 428 | 454 | 75.0 | 52.0 | 87.9 | 78.5 |

[1] On Stream Time.
[2] Reactor Catalyst Charge.
[3] Reactor Charge Density.
[4] Comparative Catalyst Comparison of the weight/weight productivity values obtained with the various shaped oxidation catalyst structures (compare Examples 1A with 1B, 1C, 1D, or 1E and 2A with 2B or 2C) clearly demonstrates the advantages of the shaped oxidation catalyst structures of the instant invention over conventional catalyst shapes. In general, a similar comparison of weight % yield of maleic anhydride demonstrates equivalent or superior performance of the shaped oxidation catalyst structures of the instant invention over the conventional prior art catalyst shapes. As a result, the combined advantage of equivalent or greater reaction yield using less catalyst (on a weight basis) provides a significant economic advantage.

Thus, it is apparent that there has been provided, in accordance with the instant invention, shaped oxidation catalyst structures that fully satisfy the objects and advantages set forth hereinabove. While the invention has been described with respect to various specific examples and embodiments thereof, it is understood that the invention is not limited thereto and many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A shaped oxidation catalyst structure for the production of maleic anhydride, which shaped structure comprises a solid geometric form having at least one (1) void space disposed in the external surface thereof, the shaped structure being characterized by (a) containing catalytic material comprised of mixed oxides of vanadium and phosphorus, and (b) exhibiting (i) a geometric volume of from about 30 percent to about 67 percent of that exhibited by the void space-free solid geometric form, (ii) an external geometric surface area/geometric volume ratio of at least about 20 cm$^{-1}$, (iii) a bulk density of from about 0.4 g/cm$^3$ to about 1.4 g/cm$^3$, and (iv)

a mechanical resistance sufficient to maintain substantially the structural integrity of the shaped structure under handling and use conditions.

2. The shaped oxidation catalyst structure of claim 1 wherein the solid geometric form is selected from the group consisting of cylinders, cubes, cones, truncated cones, pyramids, truncated pyramids, spheres, and prisms.

3. The shaped oxidation catalyst structure of claim 1 wherein the void spaces are equally spaced over the external surface in which such void spaces are located.

4. The shaped oxidation catalyst structure of claim 1 wherein the void spaces are selected from the group consisting of grooves, holes, and dimples.

5. The shaped oxidation catalyst structure of claim 1 wherein the void spaces are selected from the group consisting of angular and rounded shapes.

6. The shaped oxidation catalyst structure of claim 5 wherein the void spaces are rounded shapes.

7. The shaped oxidation catalyst structure of claim 1 wherein the geometric volume thereof is from about 40 percent to about 61 percent of that of the void space-free solid geometric form.

8. The shaped oxidation catalyst structure of claim 1 wherein the external geometric surface area/geometric volume ratio is at least 27 cm$^{-1}$.

9. The shaped oxidation catalyst structure of claim 1 wherein the bulk density thereof is from about 0.5 g/cm$^3$ to about 1.1 g/cm$^3$.

10. The shaped oxidation catalyst structure of claim 1 wherein the mechanical resistance, as determined by side crush strength, is from about 4.45 N to about 222.4 N.

11. The shaped oxidation catalyst structure of claim 10 wherein the side crush strength is from about 13.3 N to about 89 N.

12. The shaped oxidation catalyst structure of claim 1 wherein the shaped structure exhibits a base width of from about 3.175 mm to about 6.35 mm and a height/base width ratio of from about 0.5 to about 2.0.

13. The shaped oxidation catalyst structure of claim 1 wherein the catalytic material is represented by the empirical formula $$VP_xO_yM_z$$

wherein M is at least one promoter element selected from the group consisting of elements from Groups IA, IB, IIA, IIB, IIIA, IIIB, IVA, IVB, VA, VB, VIB, and VIIIB of the Periodic Table of the Elements, x is a number from about 0.5 to about 2.0, y is a number taken to satisfy the valences of V, P, and M in the oxidation states in which they exist in the composition, and z is a number from zero (0) to about 1.0.

14. The shaped oxidation catalyst structure of claim 13 wherein x is a number from about 0.95 to about 1.35 and z is a number up to about 0.5.

15. The shaped oxidation catalyst structure of claim 13 wherein M is selected from the group consisting of elements from Groups IA and IIB of the Periodic Table of the Elements.

16. The shaped oxidation catalyst structure of claim 15 wherein M from Group IA is lithium and from Group IIB is zinc.

17. The shaped oxidation catalyst structure of claim 13 wherein M is selected from the group consisting of elements from Groups IA and VIIIB of the Periodic Table of the Elements.

18. The shaped oxidation catalyst structure of claim 17 wherein M from Group IA is lithium and from Group VIIIB is iron.